United States Patent
Burnham, III et al.

[11] Patent Number: 5,907,094
[45] Date of Patent: May 25, 1999

[54] NITRIFICATION ACTIVITY TEST (NAT): PROCEDURE TO MONITOR NITRIFIER BIOMASS

[76] Inventors: Walter V. Burnham, III, 406 Tamarind, Lake Jackson; Frederic A. Jagush, 914 Glenlea Ct., Friendswood, both of Tex. 77566

[21] Appl. No.: 08/840,258

[22] Filed: Apr. 14, 1997

[51] Int. Cl.$^6$ .................................................... C02C 1/06
[52] U.S. Cl. ...................... 73/53.01; 73/61.41; 73/64.56; 210/605; 210/903
[58] Field of Search ............................... 73/53.01, 61.41, 73/64.56; 210/605, 903

[56] References Cited

FOREIGN PATENT DOCUMENTS 53-107157  9/1978  Japan .

*Primary Examiner*—Daniel S. Larkin
*Attorney, Agent, or Firm*—Joanne P. Will

[57] ABSTRACT

The present invention relates to a test procedure for evaluating nitrification activity which takes thirty minutes and accurately demonstrates a correlation of the nitrification activity when compared to ammonia nitrogen removal efficiencies. The test procedure involves treating sludge samples with an ammonium nitrogen/carbonate medium and a buffer and measuring BOD, and then adding thiourea and again measuring BOD. The nitrification activity is determined by subtracting the two BOD measurements.

1 Claim, 1 Drawing Sheet

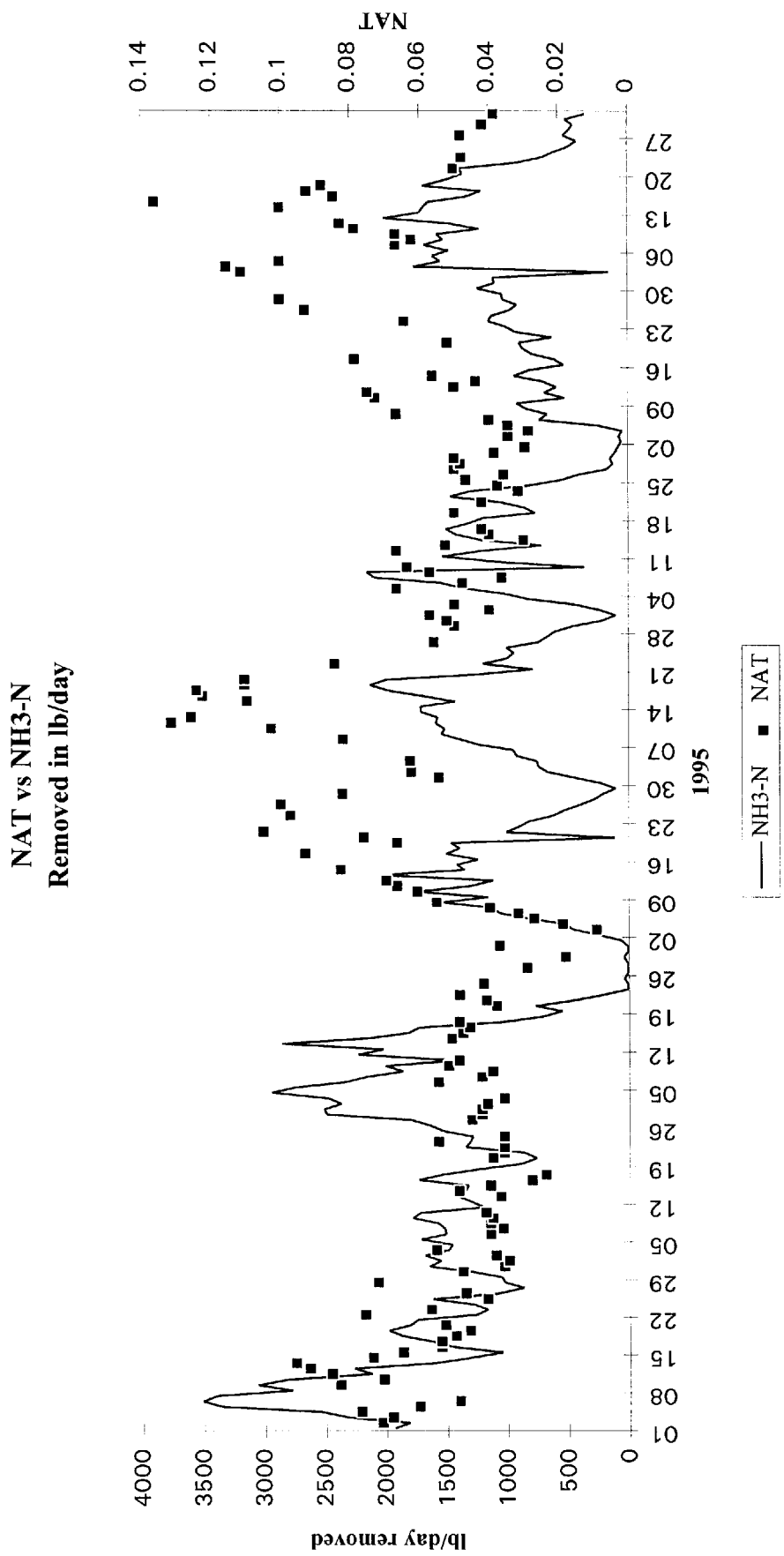

NITRIFICATION ACTIVITY TEST (NAT): PROCEDURE TO MONITOR NITRIFIER BIOMASS

FIELD OF THE INVENTION

The present invention relates to a method for assaying wastewater treatment nitrifying bacteria biomass.

BACKGROUND

Effective waste water treatment is a major concern of the industrialized world. Waste water often contains phosphorous and nitrogen which stimulates unwanted algae growth, creating unpleasant tastes and odors in the water supply; and operating problems in wastewater treatment plant. Wastewater treatment can be accomplished by physical/chemical methods or biological methods. Biological nitrification is a common biological method for removal of ammonia nitrogen in wastewater. The microorganisms involved are the nitrifying bacteria, nitrosomonas, and nitrobacter. Nitrification is the biological oxidation of ammonia nitrogen to nitrate nitrogen with nitrite nitrogen formation as an intermediate. This biological oxidation reaction produces the energy these bacteria need to assimilate inorganic carbon (IC), which is their sole carbon source for cell synthesis. See, Eckenfelder, *Industrial Water Pollution Control*, 2nd Edit. Nitrifying bacteria are sensitive to pH, temperature, heavy metals, and a number of organic and inorganic compounds. Other factors affecting nitrification performance are the amounts of dissolved oxygen (DO) and inorganic carbon (IC) in the bioreactor. Thus, the biological nitrification process can be easily upset. Traditionally, nitrifier populations are sensitive to minor operational upsets which require days to recover. This is a problem for waste water treatment facilities and usually results in an environmental excursion.

However, despite this sensitivity, the biological nitrification process remains a highly useful means for removing ammonia nitrogen in the art of wastewater treatment technology. Thus, due to the fact that nitrifying bacteria populations are easily upset, there is a need in the art for a method to quickly and accurately determine nitrifier populations. Currently, determination of nitrifier populations in an activated sludge process has been limited to estimating the concentrations based on mixed liquor concentrations and plate counts which requires seven days to complete. See, Wilson, G. S. and Miles, A. S. "Tropley and Wilson's Principles of Bacteriology and Immunity", The Williams and Wilkins Company, Baltimore, Md., 1964, pp2253–2563. Other references describing methods of determining nitrifier populations include, Carpenter, P. L., "Microbiology", W. G. Sanders Company, Philadelphia, Pa., 1961, pp 44–45 and Stanier, R. Y., Doudoroff, M. and Adelberg, E. A.; "The Microbial World", 3rd edition, Prentice Hall, Inc., New Jersey, 1970, pp 78–96; Downing, A. L., "Advances in Water Quality Improvement", Vol. 1, University of Texas Press, Austin, Tex. and Eckendelder, Wesley W., Jr., "Industrial Water Pollution Control", McGraw-Hill Book Company, 1989, pp 173–176; Metcalf and Eddy, Inc., "Wastewater Engineering: Treatment/Disposal/Reuse", 2nd edition, McGraw-Hill Book Company, 1979, pp 398–408, and Eckenfelder, Wesley W., Jr., "Principles of Water Quality Management", CBI Publishing Company, Inc., Boston, Mass., pp 317–325. The current methods are problematic, since there is no analytical basis for estimation of nitrifier populations.

Applicants' have solved the aforementioned problem in the art. Specifically, Applicants have developed the Nitrification Activity Test (NAT) to support daily wastewater treatment plant operational control with a test procedure that more accurately evaluates the nitrifier performance within a reasonable time period. The Applicants' NAT differentiates heterotrophic and autotrophic respiration rates within a thirty minute period and accurately demonstrates a correlation of the nitrification activity when compared to ammonia nitrogen removal efficiencies. The test results from the NAT procedure can be used to evaluate and control nitrification sludge age requirements and nitrification inhibition effects due to pH, temperature, dissolved oxygen levels, and varying substrates. The NAT procedure can also be used to evaluate acute toxicity in the wastewater treatment facility. The Applicants' test procedure uses standard laboratory equipment and reagents.

SUMMARY

A method for determining nitrifying bacteria activity in wastewater treatment facilities comprising the steps of:
 (1) obtaining a 600 ml sample of mixed liquor suspended solids, also known as sludge, from the bioreactor;
 (2) adding 10 mls of a medium solution comprising:
  (i) 3.5 g/L of $NH_4Cl$ and
  (ii) 10.5 g/L of $NaHCO_3$ to said sample; obtained in step (1) and also
 (3) adding 1 ml of a buffer comprising:
  (i) 0.85 g/L of $KH_2PO_4$
  (ii) 2.17 g/L of $K_2HPO_4$
  (iii) 3.34 g/L of $Na_2HPO_4.7H_2O$
  (iv) 2.25 g/L of $MgSO_4.7H_2O$
  (v) 3.6 g/L of $CaCl_2.2H_2O$ and
  (vi) 0.25 g/L of $FeCl_3$ to said wastewater sample;
 (4) aerating the wastewater sample obtained in steps (2) and (3) for one minute;
 (5) transfering 300 mls of the sample from step (4) to a Biochemical Oxygen Demand (BOD) bottle, mixing and
 (6) measuring the dissolved oxygen concentration until a concentration of 0.2 $mgO_2/L$ is obtained or the concentration has stabilized;
 (7) simultaneously adding 0.2 grams of thiourea to the remaining 300 mls from step (4) at the time when step (5) is performed;
 (8) aerating the solution obtained in step (7) for 5 minutes;
 (9) transfering the step (8) solution to a BOD bottle;
 (10) measuring the oxygen concentration as in step (6); and
 (11) calculating the nitrification activity

BRIEF DESCRIPTION OF THE DRAWINGS

FIG. 1 compares the NAT test results to the pounds per day of ammonia nitrogen removed. Specifically, the graph in FIG. 1 tracks the NAT results, which identify the important nitrifying bacteria populations, with the ammonium nitrogen removed by said nitrifying bacteria populations.

DETAILED DESCRIPTION

A method for determining nitrifying bacteria activity in wastewater treatment facilities comprising the steps of:
 (1) obtaining a 600 ml sample of mixed liquor suspended solids, also known as sludge, from the bioreactor;
 (2) adding 10 mls of a medium solution comprising:
  (i) 3.5 g/L of $NH_4Cl$ and (ii) 10.5 g/L of NaHCO$_3$ to said sample obtained in step (1); and also (3) adding 1 ml of a buffer comprising:
  (i) 0.85 g/L of KH$_2$PO$_4$
  (ii) 2.17 g/L of K$_2$HPO$_4$
  (iii) 3.34 g/L of Na$_2$HPO$_4$.7H$_2$O
  (iv) 2.25 g/L of MgSO$_4$.7H$_2$O
  (v) 3.6 g/L of CaCl$_2$.2H$_2$O and
  (vi) 0.25 g/L of FeCl$_3$ to said wastewater sample;

(4) aerating the wastewater sample obtained in steps (2) and (3) for one minute;

(5) transfering 300 mls of the sample from step (4) to a Biochemical Oxygen Demand (6) measuring the dissolved oxygen concentration until a concentration of 0.2 mgO$_2$/L is obtained or the concentration has stabilized;

(7) simultaneously adding 0.2 grams of thiourea to the remaining 300 mls from step (4) at the time when step (5) is performed;

(8) aerating the solution obtained in step (7) for 5 minutes;

(9) transfering the solution form step (8) to a BOD bottle;

(10) measuring the oxygen concentration as in step (6); and

(11) calculating the nitrification activity.

Performing the NAT

The NAT test procedure requires addition of a medium solution and buffer solution. The medium solution is a source for ammonia nitrogen and carbonates.

| The medium solution is: | (i) | 3.5 g/L NH$_4$CL and |
| --- | --- | --- |
|  | (ii) | 10.5 g/L NaHCO$_3$ |

| The buffer solution is: | (i) | 0.85 g/L of KH$_2$PO$_4$ |
| --- | --- | --- |
|  | (ii) | 2.17 g/L of K$_2$HPO$_4$ |
|  | (iii) | 3.34 g/L of Na$_2$HPO$_4$.7H$_2$O |
|  | (iv) | 2.25 g/L of MgSO$_4$.7H$_2$O |
|  | (v) | 3.6 g/L of CaCl$_2$.2H$_2$O and |
|  | (vi) | 0.25 g/L of FeCl$_3$ |

Initial Test Setup:

Take 600 ml of a test sludge from the bioreactor and add 10 ml of the medium solution and 1 ml of the buffer solution. Aerate the mixture for one minute.

Aerating is accomplished by bubbling air or oxygen into the test sludge, increasing the dissolved oxygen concentration. For example, an air pump is used to supply air to a diffusor made of 0.25 inch stainless steel tubing. The diffusor is 3.75 inches in diameter with 30 holes drilled into the bottom of the tubing. (each hole is 0.0625 inches in diameter.) This also provided adequate mixing. Measuring the oxygen uptake rate is done by recording the dissolved oxygen concentration in the sludge until the concentration is less than 0.2 mg/L or the concentration has stablized, then determining the uptake rate as follows: Initial dissolved oxygen concentration—final dissolved oxygen concentration/time of test in minutes (mgO$_2$/min).

Total Activity Setup:

Transfer 300 ml of the initial aerated setup mixture to a BOD bottle, mix and insert a dissolved oxygen probe. Measure and record the dissolved oxygen concentration until a concentration of 0.2 mgO$_2$/L is obtained. Record the time in minutes.

The NAT procedure consists of two measurements, total and heterotrophic oxygen uptake rates. The autotrophic rate is determined by the difference of these two measurements. The nitrification activity is represented by the autotrophic rate. Knowing this rate and dividing the result by the mixed liquor concentration, results in a measurement that can be applied to the process. The NAT is a simple dissolved oxygen uptake rate that differentiates between heterotrophic and autotrophic uptake rates. The Nitrification Activity Test (NAT) measures the difference between oxygen uptake rates of the total and heterotrophic bacteria (mgO2/L/min). See, APHA, AWWA, WEF, "Standard Methods For The Examination of Water and Wastewater", 18th edition 1992, Section 2, page 64.

The difference is divided by the mixed liquor concentration, in grams, of the test solution. The unit is expressed as mgO$_2$/gMLSS/min of the nitrifying or autotrophic biomass. MLSS as used herein refers to "mixed liquor suspended solids".

Heterotrophic Activity:

As soon as the total activity setup is started, add 0.2 grams of thiourea to the remaining 300 ml of test sludge and aerate concurrently while the total activity uptake is being performed. After the total activity test is completed, remove the mixture and transfer the aerated mixed liquor/thiourea mixture to the BOD bottle. Mix and insert the dissolved oxygen probe and repeat the dissolved oxygen measurement. The uptake will not include the nitrifiers, since they have been inhibited by the thiourea.

Autotrophic Activity Determination (Nitrification Activity Test):

| NAT | = | total activity rate (mg/L/min) - heterotrophic activity rate (mg/L/min)/MLSS in g/L |
| --- | --- | --- |
|  | = | mgO$_2$/gMLSS/min |

For the mixed liquor used in the procedure development, the NAT results normally ranged from 0.04 to 0.20. Every system will have to be evaluated to determine its control range.

Further, it is preferable that the NAT be setup within a period of ten minutes after the mixed liquor sample is removed from the aeration basin or bioreactor. Exceeding this time period was found to lower the total oxygen uptake results. Other variables effecting oxygen uptake results are field and laboratory temperatures.

The normal uptake rates for the inventors' facility ranged from 0.04 to 0.20 mg O2/gMLSS/min. The variance in the results was due to the operation of different aeration systems, (high speed floating areators vs membrane diffusor systems), and ammonia nitrogen feed rates fluctuations in production. For example, the ammonia nitrogen feed rate was three pounds per minute for two weeks, then 0.5 pounds per minute for two weeks. In addition, 65% of the treatment volume has high speed floating aerators and 35% membrane diffusor systems. This required extremely tight controls on the reactor parameters for maintaining the nitrifier activity. The attached graph, FIG. 1, compares the NAT results to the pounds per day of ammonia nitrogen removed. The NAT's were also used to note nitrifier population acclimation progress.

Specifically, FIG. 1 compares the NAT test results to the pounds per day of ammonia nitrogen removed. Specifically, the graph in FIG. 1 tracks the NAT results, which identify the important nitrifying bacteria populations, with the ammonium nitrogen removed by said nitrifying bacteria populations.

We claim:

1. A method for determining nitrifying bacteria activity in the bioreactor in wastewater treatment facilities wherein the oxygen concentration of aerated sludge is measured comprising the steps of:
   (1) obtaining a 600 ml sample of mixed liquor suspended solids, also known as sludge from said bioreactor;
   (2) adding 10 mls of a medium solution, to the 600 ml sample obtained in step (1), comprising:
      (i) 3.5 g/L of $NH_4Cl$ and
      (ii) 10.5 g/L of $NaHCO_3$ to said sludge sample; and also
   (3) adding 1 ml of a buffer, to the 600 ml sample obtained in step (1), comprising:
      (i) 0.85 g/L of $KH_2PO_4$,
      (ii) 2.17 g/L of $K_2HPO_4$,
      (iii) 3.34 g/L of $Na_2HPO_4*7H_2O$,
      (iv) 2.25 g/L of $MgSO_4*7H_2O$,
      (v) 3.6 g/L of $CaCl_2.2H_2O$, and
      (vi) 0.25 g/L of $FeCl_3$ to said sludge sample;
   (4) aerating the wastewater sample obtained in steps (2) and (3) for one minute;
   (5) transferring 300 mls of the sample obtained from steps (1), (2) and (3) to a Biochemical Oxygen Demand (BOD) bottle, mixing and
   (6) measuring the dissolved oxygen concentration of the sludge sample obtained in step (1) and treated in steps (2), (3) and (4) until a concentration of 0.2 $mgO_2/L$ is obtained or a concentration has stabilized;
   (7) simultaneously adding 0.2 grams of thiourea to the remaining 300 mls from step (4) at the time when step (5) is performed;
   (8) aerating the solution obtained in step (7) for 5 minutes;
   (9) transferring the solution from step (8) to a BOD bottle;
   (10) measuring the oxygen concentration as in step (6); and
   (11) calculating the nitrification activity by subtracting the oxygen concentration obtained in step (6) from the oxygen concentration obtained in step (10).

* * * * *